United States Patent [19]
Roger

[11] Patent Number: 5,961,521
[45] Date of Patent: Oct. 5, 1999

[54] SURGICAL SCREW AND WASHER

[75] Inventor: Gregory James Roger, Sydney, Australia

[73] Assignee: Smith & Nephew, Inc., Andover, Mass.

[21] Appl. No.: 09/023,343

[22] Filed: Feb. 13, 1998

Related U.S. Application Data

[63] Continuation of application No. 08/553,718, Feb. 20, 1996, Pat. No. 5,718,706.
[51] Int. Cl.$^6$ .................................................. A61B 17/064
[52] U.S. Cl. .......................... 606/73; 606/232; 606/151; 606/213; 606/224
[58] Field of Search ............................. 606/73, 151, 158, 606/157, 213, 216, 219, 224, 225, 232

[56] References Cited

U.S. PATENT DOCUMENTS

| | | |
|---|---|---|
| 2,242,003 | 5/1941 | Lorenzo . |
| 2,267,925 | 12/1941 | Johnston . |
| 4,463,753 | 8/1984 | Gustilo . |
| 4,537,185 | 8/1985 | Stednitz . |
| 4,744,793 | 5/1988 | Parr et al. . |
| 4,772,286 | 9/1988 | Goble et al. . |

(List continued on next page.)

FOREIGN PATENT DOCUMENTS

| | | |
|---|---|---|
| 14615/28 | 7/1928 | Australia . |
| 59999/90 | 2/1991 | Australia . |
| 0172130 | 2/1986 | European Pat. Off. . |
| 0241792 | 10/1987 | European Pat. Off. . |
| 0260970 | 3/1988 | European Pat. Off. . |
| 0282789 | 9/1988 | European Pat. Off. . |

(List continued on next page.)

OTHER PUBLICATIONS

European Patent Abstracts, Week 9240, p. 235, EP 506420–A1.
European Patent Abstracts, Week 9240, p. 189, EP 506213–A1.
European Patent Abstracts, Week 9237, p. 161, EP 502698–A1.
European Patent Abstracts, Week 9212, p. 267, EP 475–889–A.
European Patent Abstracts, Week 9208, p. 99, EP 471–419–A.
European Patent Abstracts, Week 9206, p. 99, EP 469–441–A.
European Patent Abstacts, Week 9144, p. 250, EP 454–601–A.
European Patent Abstracts, Week 9143, p. 28, EP 452–442–A.
European Patent Abstracts, Week 9106, p. 29, EP 411–109–A.
European Patent Abstracts, Week 9118, p. 74, EP 424–734–A.
European Patent Abstracts, Week 9133, p. 77, EP 440–991–A.
European Patent Abstracts, Week 9133, EP 441–065–A.
European Patent Abstracts, Week 9134, p. 177, EP 442–629–A.

(List continued on next page.)

*Primary Examiner*—Michael Buiz
*Assistant Examiner*—Daphna Shai
*Attorney, Agent, or Firm*—Fish & Richardson, PC

[57] ABSTRACT

A surgical fastener for fixation of graft tendon in a bone hole comprising a screw having a head, neck, and shank, and a washer disposed about the neck. The tendon is attached to the washer so as to ensure that the tendon is immobilised between the head of the screw and the wall of the bone hole thereby reducing pistoning under load and reducing graft failure. In one embodiment, the fastener includes a bone plug disposed about the neck of the screw between the head and the washer, the neck being adapted to laterally press the bone plug and thereby immobilise a tendon attached to the washer between the bone plug and the wall of the bone hole. In another embodiment, the invention consists in a surgical staple having two substantially parallel legs, a transverse head member and a washer which holds a loop of tendon under the staple when it is inserted into a bone.

14 Claims, 3 Drawing Sheets

U.S. PATENT DOCUMENTS

| | | |
|---|---|---|
| 4,775,380 | 10/1988 | Seedhom et al. . |
| 4,828,562 | 5/1989 | Kenna . |
| 4,870,957 | 10/1989 | Goble et al. . |
| 4,927,421 | 5/1990 | Goble et al. . |
| 4,950,270 | 8/1990 | Bowman et al. . |
| 4,988,351 | 1/1991 | Paulos et al. . |
| 5,084,050 | 1/1992 | Draenert . |
| 5,116,337 | 5/1992 | Johnson . |
| 5,129,902 | 7/1992 | Goble et al. . |
| 5,129,906 | 7/1992 | Ross et al. . |
| 5,139,520 | 8/1992 | Rosenberg . |
| 5,209,753 | 5/1993 | Biedermann et al. . |
| 5,211,647 | 5/1993 | Schmieding . |
| 5,246,441 | 9/1993 | Ross et al. . |
| 5,281,422 | 1/1994 | Badylak et al. . |
| 5,285,040 | 2/1994 | Bruchman et al. . |
| 5,383,878 | 1/1995 | Roger et al. ............................. 606/73 |
| 5,443,468 | 8/1995 | Johnson . |
| 5,443,509 | 8/1995 | Boucher et al. . |
| 5,454,811 | 10/1995 | Huebner . |
| 5,456,685 | 10/1995 | Huebner . |
| 5,470,334 | 11/1995 | Ross et al. . |
| 5,628,766 | 5/1997 | Johnson . |
| 5,632,748 | 5/1997 | Beck et al. . |
| 5,674,224 | 10/1997 | Howell et al. . |

FOREIGN PATENT DOCUMENTS

| | | |
|---|---|---|
| 0317406 | 5/1989 | European Pat. Off. . |
| 0374088 | 6/1990 | European Pat. Off. . |
| 451932A1 | 4/1991 | European Pat. Off. . |
| 2622790 | 5/1989 | France . |
| 8916764 | 6/1991 | France . |
| 2687911 | 9/1993 | France . |
| 2688689 | 9/1993 | France . |
| 2704140A3 | 10/1994 | France . |
| 2529669 | 3/1976 | Germany . |
| 2747312 | 4/1979 | Germany . |
| 2818254 | 10/1979 | Germany . |
| 4127550 | 2/1993 | Germany . |
| 5300917 | 11/1993 | Japan . |
| WO89/09030 | 10/1989 | WIPO . |
| WO 90/00370 | 1/1990 | WIPO . |
| WO90/08510 | 8/1990 | WIPO . |
| WO92/03980 | 3/1992 | WIPO . |

OTHER PUBLICATIONS

Kurosaka, M. et al., Am. Journal of Sports Med., vol. 15, No. 3, pp. 225–229, "A Biochemical Comparison of Different Surgical Techniques of Graft Fixation in Anterior Cruciate Ligament Reconstruction."

Lambert K.L., Clinical Orthopedics and Related Research, No. 72, Jan./Feb. 1983, pp. 85–89, "Vascularized Patella Tendon Graft with Rigid internal Fixation for Anterior Cruciate Ligament Insufficiency."

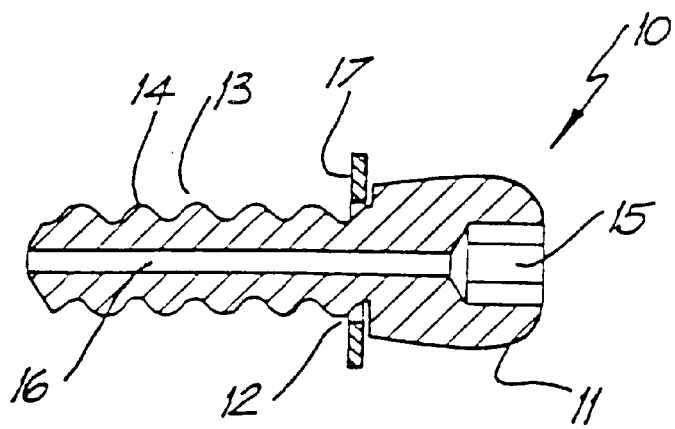
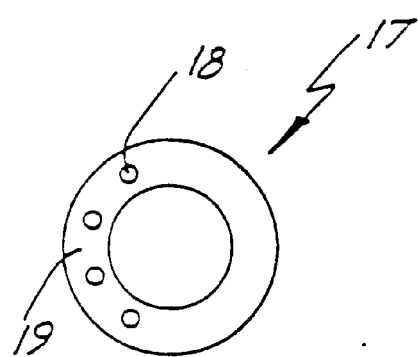
FIG. 1    FIG. 2
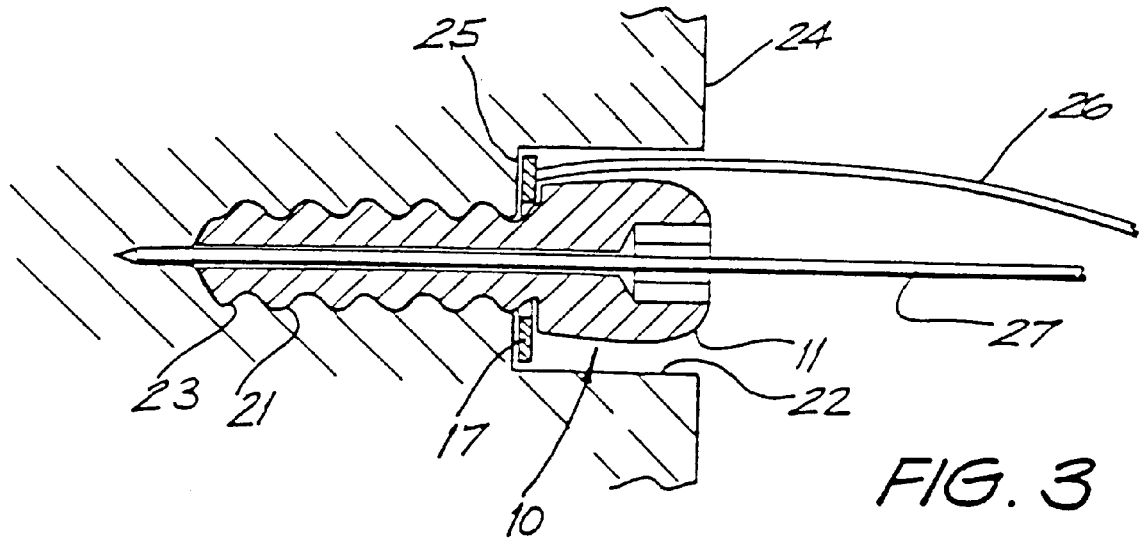
FIG. 3
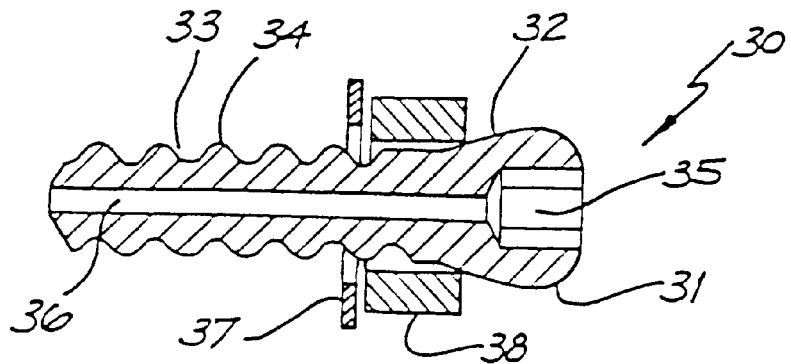
FIG. 4

SURGICAL SCREW AND WASHER

This application is a continuation of Ser. No. 08/553,718 filed Feb. 20, 19996, now U.S. Pat. No. 5,718,706.

FIELD OF THE INVENTION

The present invention relates generally to a fastener for attaching tendons to bones and in particular to a surgical screw having a washer for immobilising tendons within pre-formed holes in bone.

BACKGROUND ART

It is known that damaged anterior cracked ligaments can be repaired by grafting a portion of patellar tendon, which has been harvested with blocks of bone physiologically bound at each end, between the femur and tibia at the knee joint. The harvested blocks of bone are typically positioned in pre-drilled holes in the femur and tibia.

This method of ligament repair is often a difficult and time consuming operation with consequent concerns about patient comfort and safety. The harvesting of patellar tendon can also itself cause problems for the patient. In many patients the graft tendon is also often not in a suitable physiological condition for use. It is, therefore, desirable to harvest tendon without bone attached and then position the tendon at the required site such that the bone growth fixates the tendon to the bone.

A main requirement for fixation is that the graft tendon be held securely without moving or pistoning within a bone hole.

Current methods for fixation of a tendon include a staple, around which the tendon is positioned prior to the staple being placed within the bone. This method suffers two main disadvantages. Firstly, on the femoral side, the staple is applied to the outer surface of the femur and an extra incision is therefore required. Secondly, because fixation is outside the femur and the tendon lies in a bone tunnel of around 40 mm in length, the elasticity of the tendon allows pistoning under load and so healing to the bone of the tendon graft may fail or be a weak, fibrous healing that allows later loosening.

DISCLOSURE OF THE INVENTION

According to one aspect of the present invention consists in a surgical fastener for attaching one end of a graft tendon to a bone, the bone having a hole formed therein to receive the surgical fastener, the surgical fastener being a screw having a head, a neck and a shank with an end distal the head, the shank having a thread formed along at least a portion of its length, the head being generally hemispherical and of a diameter greater than the shank, and a an annular washer being disposed about the neck of the screw intermediate the head and shank, wherein the washer is arranged such that in operation the one end of the tendon can be attached thereto and substantially immobilised between the head and the inside of the hole.

The thread in longitudinal section along the entirety of the thread is preferably devoid of an outermost cutting line. In one embodiment the screw has a shank having a thread formed along the entirety of the shank. The screw thread is preferably approximately or wholly sinusoidal in longitudinal section so as to present a soft thread devoid of an outermost cutting line.

The screw preferably has a drive socket concentric with the head and a longitudinal cannulation concentric of the shank.

In a further embodiment the annular washer is positioned adjacent the head of the screw and preferably has at least one hole in its annular portion. The washer more preferably has four holes in its annular portion, the four holes preferably confined to one half of the annular portion.

In a second aspect an annular plug made of bone is disposed about the neck of the screw between the annular washer and the head. The neck of the screw in this embodiment is preferably adapted such that the bone plug is compressed laterally when the screw is in use.

In a further embodiment the present invention comprises a method for attaching one end of a tendon to a bone, using the surgical fastener according to the first aspect of the invention, comprising the steps of:

(a) forming a hole in the bone, the hole having a first end and a second end and comprising two portions, the first portion, adjacent the first end, having a diameter larger than the diameter of the second portion, distal to the first end, such that there is formed an annular abutment in the hole;

(b) attaching the one end of the tendon to the washer;

(c) drawing the washer with the tendon attached into the hole such that the washer is positioned proximate the annular abutment; and (d) screwing the surgical screw into the hole such that the washer is abutted with the annular abutment and the tendon is immobilised with the head of the screw forcing the tendon into abutment with the bone within the first portion of the hole.

The tendon preferably has sutures secured to its one end, the sutures being preferably tied to one or more holes in the annular portion of the washer. The sutures are more preferably tied to four holes in the washer, the four holes being preferably confined to one half of the annular portion.

The surgical screw is preferably of a length such that the one end of the shank reaches the outer cortex of the bone when the screw is screwed into the bone. The screw is preferably inserted using the drive socket.

The bone is preferably a femur and the hole in the bone is preferably formed in the femoral condyle by a drill bit.

The screw is preferably cannulated so as to accept large diameter Kirschner wires or the like that allow accurate guiding of the screw arthroscopically.

In another embodiment the present invention comprises a method for attaching one end of a tendon to a bone, using the surgical fastener according to the second aspect of the invention, comprising the steps of:

(a) forming a hole in the bone;

(b) attaching the one end of the tendon to the annular washer;

(c) positioning the washer concentrically and proximate one end of the annular bone plug;

(d) inserting the washer and the bone plug into the hole using an insertion means such that the washer is distal the entrance of the hole; and (e) screwing the surgical screw into the hole such that the bone plug is laterally compressed, thereby immobilising the tendon between the wall of the hole and a substantial portion of the length of the bone plug.

In a preferred embodiment of the invention, the annular bone plug prior to insertion in the bone hole is mounted in a holder, the holder having a first and second end and preferably surrounding the bone plug. In a more preferred embodiment the washer and bone plug are both mounted in the holder such that the tendon attached to the washer lies substantially longitudinally along the length of the bone plug. The holder preferably has a bulge proximate the washer and bone plug to accommodate the tendon.

The insertion means preferably comprises a plunger positioned at the second end of the holder that is adapted to expel the bone plug and washer from the holder into the bone hole.

The annular washer, bone plug, holder and surgical screw are preferably positioned on a guide wire centrally positioned within the hole.

According to a third aspect, the present invention consists in a surgical fastener, the fastener being a staple for attaching a graft tendon to a bone, the surgical staple comprising two substantially parallel legs interconnected by a transverse head member, each leg being of substantially the same length and having a free end portion connected substantially at a right angle to a head portion, such that the head member is laterally displaced from the free end portions and a washer disposed around the free end portions proximate the right angle connection with the head portions.

The surgical staple preferably has two parallel legs, each leg of the same length and having a free end portion connected at a right angle to a head portion.

The transverse head member interconnecting the two head portions is preferably canted downwardly from the plane of the head portions.

The surgical staple is preferably comprised of one linear member folded to the required shape. The linear member is preferably a wire with the free end portions preferably having a sharp arrow tip to facilitate insertion of the staple into the bone. The portions of the wire likely to come into contact with the tendon are preferably rounded to prevent damage to the tendon. The wire is preferably a biologically inert metal.

The washer is preferably oval in shape with rounded edges to prevent damage to the graft tendon. There are preferably two holes laterally displaced in the washer for each of the legs. The washer is preferably made of a biologically inert metal.

In a further embodiment the present invention comprises a method for attaching a loop of tendon to a bone using the surgical fastener according to the third aspect of the invention comprising the steps of:

(a) positioning the washer through the loop of the tendon;
(b) inserting the free end portions of the staple's legs through the washer so as to position the loop of tendon within the staple; and
(c) inserting the staple into the bone such that the tendon is firmly secured to the bone both under the washer and under the laterally displaced head member, such that any tilting of the staple under load will serve to press the head member more firmly onto the tendon thereby ameliorating loosening of the tendon and staple from the bone.

The staple is preferably inserted into the bone at the required site using an appropriate hammer like tool.

BRIEF DESCRIPTION OF THE DRAWINGS

By way of example only, preferred embodiments of the invention will be described with reference to the accompanying drawings, in which;

FIG. 1 is a longitudinal sectional view of one embodiment of the surgical fastener of the present invention;

FIG. 2 is a plan view of one embodiment of the annular washer of the present invention;

FIG. 3 is a longitudinal sectional view of the surgical screw and washer of FIG. 1 and FIG. 2 respectively, after insertion in a bone;

FIG. 4 is a longitudinal sectional view of a second embodiment of the surgical fastener;

DETAILED DESCRIPTION AND PREFERRED EMBODIMENT

Figure 5:
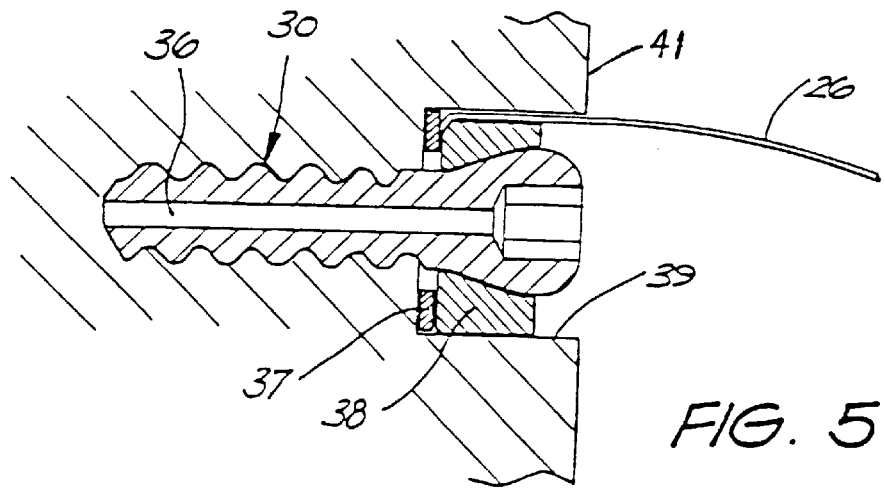
FIG. 5 is a longitudinal sectional view of the surgical screw of FIG. 4 after insertion into a bone.

A surgical screw for attaching graft tendon to bone is generally shown as 10 in FIG. 1.

The surgical screw 10 includes a generally hemispherical head 11, a neck 12 and a shank 13. The shank 13 has a thread 14 that is approximately sinusoidal in longitudinal section so as to present a soft thread devoid of an outermost cutting line. An hexagonal drive socket 15 is concentrically positioned within the head 11. The screw 10 also has a central cannulation 16 along the length of the screw 10.

An annular washer 17 is disposed about the neck 12 of the screw 10. As is more clearly depicted in FIG. 2, the annular washer 17 has four holes 18 in its annular portion 19. The holes 18 are confined to one half of the annular portion 19.

The position of the surgical screw 10 when attaching a tendon to a bone is generally depicted in FIG. 3.

In order to attach a tendon using the screw 10 and washer 17 of FIG. 1 and FIG. 2, a hole 21 comprised of two portions 22 and 23, is firstly drilled into the bone 24. The first portion 22 has a diameter larger than that of the second portion 23 such that an annular abutment 25 is formed in the hole 21.

A tendon 26 having sutures secured to one end (not depicted) is then tied to the washer 17 using the holes 18. The washer 17 with the tendon 26 attached is then drawn into the hole 21 around the guide wire 27 such that the washer 17 is positioned proximate the annular abutment 25.

The surgical screw 10 is then screwed into the hole 21, guided by the central guide wire 27 such that the washer 17 is forced into abutment with the annular abutment 25. The tendon 26 is also immobilised against the wall of the first portion 22 of the hole 21 by the head 11 of the screw 10.

A second embodiment of the surgical screw is generally shown as 30 in FIG. 4.

The surgical screw 30 includes a head 31, a tapered neck 32 and a shank 33. The shank 33 has a thread 34 that is approximately sinusoidal in longitudinal section so as to present a soft thread devoid of an outermost cutting line. An hexagonal drive socket 35 is concentrically positioned within the head 31. The screw 30 also has a central cannulation 36 along the length of the screw 30.

An annular washer 37 is disposed about the neck 32 of the screw 30. An annular bone plug 38 is disposed about the neck 32 between the washer 37 and the head 31.

The position of the surgical screw 30 when attaching a tendon to a bone is generally depicted in FIG. 5.

In this embodiment, when the screw 30 is screwed into the hole 39 in the bone 41, the bone plug 38 is laterally compressed thereby immobilising the tendon 26 that is attached to the washer 37 against the wall of the hole 39. The immobilisation of the tendon 26 between the bone plug 38 and the wall of the hole 39 ensures good fixation of the tendon 26 to the bone 41, thereby reducing pistoning of the tendon and healing time.

Figure 6:
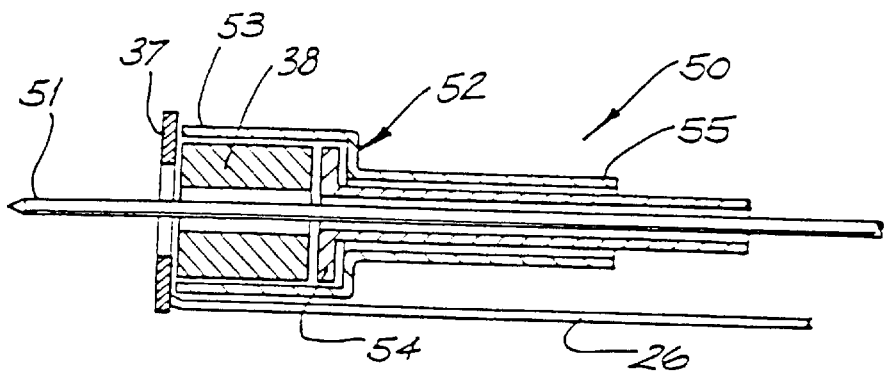
FIG. 6 is a longitudinal sectional view of one embodiment of the bone plug holder.

In order to insert the bone plug 38 and washer 37 into the hole 39, an apparatus generally shown as 50 in FIG. 6 is employed.

Prior to insertion of the bone plug 38 and washer 37 into the hole 39, a guide wire 51 is centrally positioned within the hole 39. A holder 52 is then positioned on the guide wire 51. The holder 52 is a cylindrical sleeve into which the bone plug 38 is inserted. The bone plug 38 is cannulated and, therefore, slides along the guide wire 51 into the holder 52.

A washer 37 to which a tendon 26 is attached is then slid over the guide wire 51 and positioned proximate one end 53 of the holder 52. An insertion means comprising a plunger 54 mounted at the other end 55 of the holder 52 expels the bone plug 38 from the holder 52 into the hole 39 along the guide wire 51. The washer 37 to which the tendon 26 is attached, is positioned before the bone plug 38 and is, therefore, inserted into the hole 39 ahead of the bone plug 38.

Once the washer 37 and bone plug 38 are positioned in hole 39 the plunger 54 is retracted and the holder 52 is removed from the guide wire 51.

After removal of the holder 52, the surgical screw 30 is then slid over the guide wire 51 and screwed into the hole 39. The neck 32 of the screw 30 compresses the bone plug 38 thereby immobilising the tendon 26 between the bone plug 38 and the wall of the hole 39.

Figure 7:
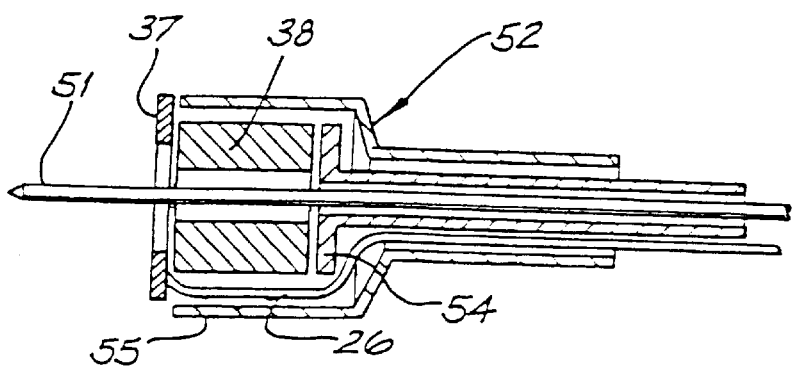
FIG. 7 is a longitudinal sectional view of another embodiment of the bone plug holder.
Figure 8:
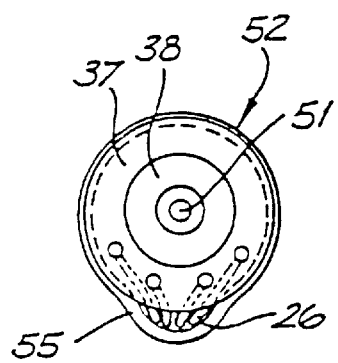
FIG. 8 is an end elevational view of the holder of FIG. 7.

Another embodiment of the holder 52 is depicted in FIG. 7 and FIG. 8. In this embodiment of the holder 52, a bulge 55 is provided on one side of the sleeve of the holder 52. Using this embodiment of the holder 52, the bone plug 38 and washer 37 to which a tendon 26 is attached are both inserted in the holder 52. The tendon 26 is positioned substantially longitudinally along the bone plug 38 and is accommodated within the bulge 55 of the holder 52.

Figure 9:
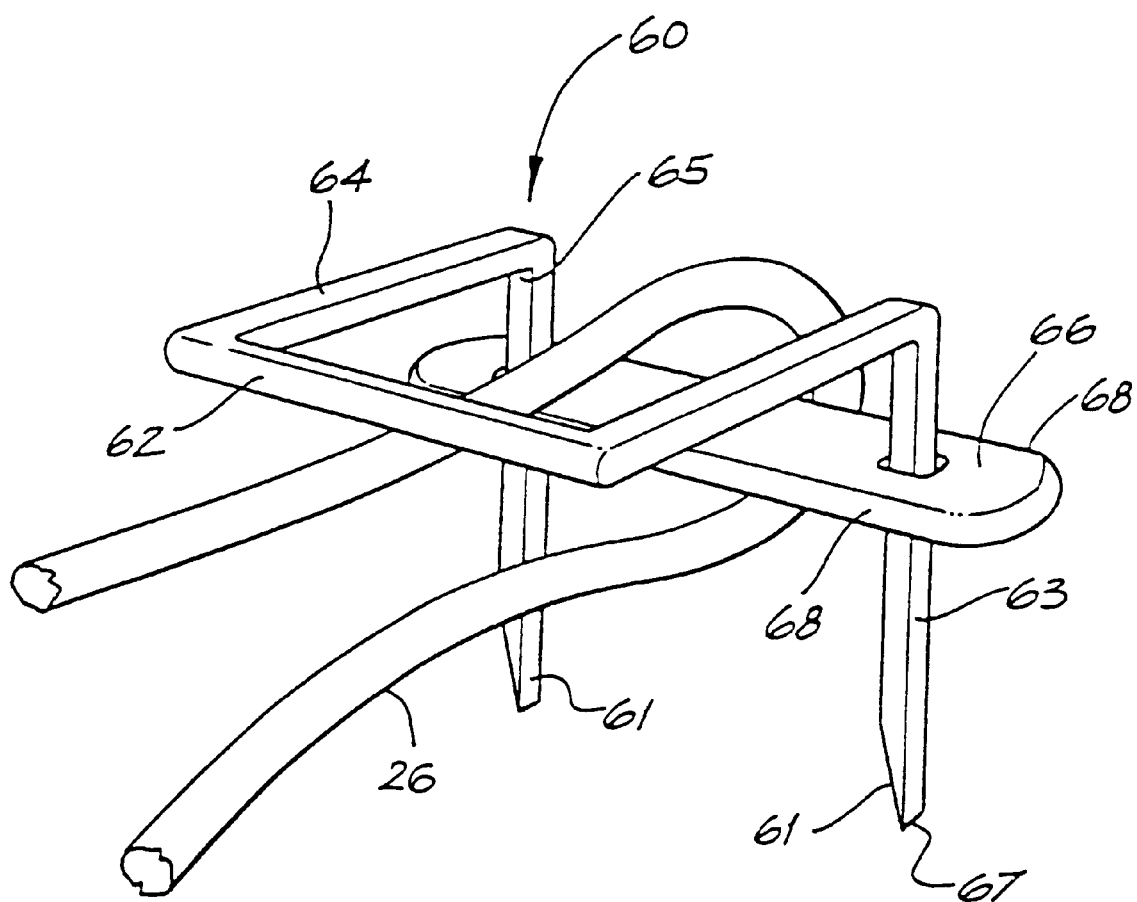
FIG. 9 is a perspective view of another embodiment of a surgical fastener.

A third embodiment of the present invention is generally shown as 60 in FIG. 9.

The surgical staple 60 includes two parallel legs 61 inter-connected by a rounded transverse head member 62.

Each of the legs 61 comprises a free end portion 63 and a head portion 64 connected at right angles 65, such that the head member 62 is laterally displaced from the free end portion 63 of the legs 61. The surgical staple 60 also includes a washer 66 disposed around the free end portions 63 proximate the right angles 65 in the legs 61.

The free end portions have an arrow shaped tip 67 to facilitate insertion of the staple 60 into the bone.

The washer 66 is oval in shape with rounded edges 68 to prevent damage to the tendon 26 which is looped around the washer 66.

In order to secure the tendon 26 to a bone, the staple 60 is hammered into a bone, with the tendon 26 secured both at the site of the washer 66 and the transverse head member 62.

Any loosening of the staple 60 under load serves to further press the transverse head member 62 more firmly onto the tendon 26 thereby ameliorating any loosening of the tendon 26 from the bone.

It will be appreciated by persons skilled in the art that numerous variations and/or modifications may be made to the invention as shown in the embodiments without departing from the spirit or scope of the invention as broadly described. The present embodiments are, therefore, to be considered in all respects as illustrative and not restrictive.

I claim:

1. A surgical fastener, the fastener being a surgical staple for attaching a graft tendon to a bone, the surgical staple comprising two substantially parallel legs interconnected by a transverse head member, each leg having a free end portion connected substantially at a right angle to a head portion connected to the transverse head member, such that the transverse head member is laterally displaced from a plane defined by the free end portions, the fastener further comprising a washer disposed around the free end portions proximate the right angle connections with the head portions.

2. The surgical fastener of claim 1 wherein the surgical staple has two parallel legs, each leg of the same length and having a free end portion connected at a right angle to a head portion.

3. The surgical fastener of claim 1 wherein the transverse head member interconnecting the two head portions is canted downwardly from the plane of the head portions.

4. The surgical fastener of any one of claim 1 wherein the surgical staple is comprised of one linear member folded to the required shape.

5. The surgical fastener of claim 4 wherein the linear member is a wire with the free end portions having a sharp arrow tip to facilitate insertion of the staple into the bone and the portions of the wire likely to come into contact with the tendon are rounded to prevent damage to the tendon.

6. The surgical fastener of any one of claim 1 wherein the washer is oval in shape with rounded edges to prevent damage of the graft tendon and has two holes laterally displaced for each of the legs.

7. A method for attaching a loop of tendon to a bone using a surgical fastener comprising a staple comprising two substantially parallel legs interconnected by a transverse head member, each leg having a free end portion connected substantially at a right angle to a head portion connected to the transverse head member, such that the transverse head member is laterally displaced from a plane defined by the free end portions, the fastener further comprising a washer disposed around the free end portions proximate the right angle connection with the head portions, the method comprising the steps of:

(a) positioning the washer through the loop of the tendon;

(b) inserting the free end portions of the legs through the washer so as to position the loop of tendon within the staple; and (c) inserting the staple into the bone such that the tendon is firmly secured to the bone both under the washer and under the laterally displaced head member, such that any tilting of the staple under load will serve to press the head member more firmly onto the tendon thereby ameliorating loosening of the tendon and staple from the bone.

8. The method of claim 7 wherein the staple is inserted into the bone at the required site using an appropriate hammer like tool.

9. A surgical staple for attaching a graft tendon to a bone, the surgical staple comprising:

a first leg comprising a first free end portion and a first head portion, wherein the first free end portion is connected to the first head portion at a substantially right angle;

a second leg comprising a second free end portion and a second head portion, wherein the second free end portion is connected to the second head portion at a substantially right angle;

a transverse head member having a first end and a second end, wherein the first end is connected to an end of the first head portion remote from the first free end portion at a substantially right angle and the second end is connected to an end of the second head portion remote from the second free end portion at a substantially right angle; and a washer disposed around the free end portions proximate the right angle connection with the head portions, wherein the first and second legs are substantially parallel and the transverse head member is laterally displaced from a plane defined by the free end portions.

10. The surgical staple of claim 9, wherein the surgical staple has two parallel legs, each leg of the same length and having the free end portion connected at a right angle to the head portion.

11. The surgical staple of claim 9, wherein the transverse head member interconnecting the two head portions is canted downwardly from a plane defined by the head portions.

12. The surgical staple of claim 9, wherein the surgical staple comprises one linear member folded to the required shape.

13. The surgical staple of claim 12, wherein the linear member is a wire with the free end portions having sharp arrow tip to facilitate insertion of the staple into the bone and the portions of the wire likely to come into contact with the tendon being rounded to prevent damage to the tendon.

14. The surgical staple of claim 9, wherein the washer is oval in shape with rounded edges to prevent damage of the graft tendon and has two holes laterally displaced for each of the legs.

* * * * *

UNITED STATES PATENT AND TRADEMARK OFFICE
CERTIFICATE OF CORRECTION

PATENT NO. : 5,961,521
APPLICATION NO. : 09/023343
DATED : October 5, 1999
INVENTOR(S) : Gregory J. Roger It is certified that error appears in the above-identified patent and that said Letters Patent is hereby corrected as shown below:

On the Title Page of the patent insert

Item
--[86] PCT No.: PCT/AU94/00296  3 June 1994

Item
[30] Foreign Application Priority Data
June 3, 1993  [AU]  Australia..............PL 9200--

Col. 6, claim 4, line 20, after "fastener of" delete --any one of--.

Col. 6, claim 6, line 28, after "fastener of" delete --any one of--.

Signed and Sealed this

Twenty-eighth Day of August, 2007

JON W. DUDAS
*Director of the United States Patent and Trademark Office*